(12) United States Patent
Kremer et al.

(10) Patent No.: US 10,991,355 B2
(45) Date of Patent: Apr. 27, 2021

(54) DYNAMIC SOUND MASKING BASED ON MONITORING BIOSIGNALS AND ENVIRONMENTAL NOISES

(71) Applicant: BOSE CORPORATION, Framingham, MA (US)

(72) Inventors: Kathleen Elizabeth Kremer, Southborough, MA (US); Jeffrey M. Ellenbogen, Towson, MD (US); Matthew Chace Carpenter, North Attleboro, MA (US); Steven Carl Pletcher, Hopkinton, MA (US); Chia-Ling Li, Framingham, MA (US)

(73) Assignee: BOSE CORPORATION, Framingham, MA (US)

( * ) Notice: Subject to any disclaimer, the term of this patent is extended or adjusted under 35 U.S.C. 154(b) by 0 days.

(21) Appl. No.: 16/278,322

(22) Filed: Feb. 18, 2019

(65) Prior Publication Data
US 2020/0265823 A1 Aug. 20, 2020

(51) Int. Cl.
*H04R 29/00* (2006.01)
*G10K 11/175* (2006.01)

(52) U.S. Cl.
CPC ......... *G10K 11/175* (2013.01); *H04R 29/001* (2013.01); *A61M 2205/50* (2013.01)

(58) Field of Classification Search
CPC ................ G10K 11/175; A61M 21/02; A61M 2021/0027; A61M 2205/3375; H04R 29/001

(Continued)

(56) References Cited

U.S. PATENT DOCUMENTS 5,444,786 A 8/1995 Raviv
9,191,744 B2 11/2015 Anderson
(Continued)

FOREIGN PATENT DOCUMENTS

EP 1 886 707 A1 2/2008
WO 2020086169 A2 4/2020

OTHER PUBLICATIONS

International Search Report and Written Opinion for International Application No. PCT/US2020/018337 dated Jun. 9, 2020, 12 pp.
(Continued)

*Primary Examiner* — Katherine A Faley
(74) *Attorney, Agent, or Firm* — Patterson + Sheridan, LLP (57) ABSTRACT

Aspects of the present disclosure provide methods, apparatuses, and systems for closed-loop sleep protection and/or sleep regulation. According to an aspect, sleep disturbing noises are predicted and a biosignal parameter is measured to dynamically mask predicted disturbing environmental noises in the sleeping environment with active attenuation. Environmental noises in a sleeping environment of a subject are detected, input, or predicted based on historical data of the sleeping environment collected over a period of time. The biosignal parameter is used to determine sleep physiology of a subject. Based on the environmental noises in the sleeping environment and the determined sleep physiology, the noises are predicted to be disturbing or non-disturbing noises. For predicted disturbing noises, one or more actions are taken to regulate sleep and avoid sleep disruption by using sound masking prior to or concurrently with the occurrence of the predicted disturbing noises.

20 Claims, 4 Drawing Sheets

(58) Field of Classification Search
USPC .................................................. 381/57, 73.1
See application file for complete search history.

(56) References Cited

U.S. PATENT DOCUMENTS

| | | |
|---|---|---|
| 9,579,060 B1 | 2/2017 | Lisy et al. |
| 10,791,986 B1 | 10/2020 | Kahn et al. |
| 2004/0234080 A1 | 11/2004 | Hernandez et al. |
| 2007/0173730 A1 | 7/2007 | Bikko |
| 2008/0097764 A1* | 4/2008 | Grill .................. G10L 19/0212 704/500 |
| 2008/0243014 A1 | 10/2008 | Moussavi et al. |
| 2009/0147965 A1 | 6/2009 | Kuo |
| 2010/0258123 A1 | 10/2010 | Somaiya et al. |
| 2010/0283618 A1 | 11/2010 | Wolfe et al. |
| 2011/0295083 A1 | 12/2011 | Doelling et al. |
| 2014/0051938 A1 | 2/2014 | Goldstein et al. |
| 2015/0194144 A1* | 7/2015 | Park ..................... G10K 11/175 381/73.1 |
| 2015/0258301 A1 | 9/2015 | Trivedi et al. |
| 2015/0281829 A1 | 10/2015 | Gauger, Jr. et al. |
| 2015/0294662 A1* | 10/2015 | Ibrahim ........... G10K 11/17885 381/71.6 |
| 2015/0320588 A1 | 11/2015 | Connor |
| 2016/0015315 A1 | 1/2016 | Auphan et al. |
| 2016/0217672 A1 | 7/2016 | Yoon et al. |
| 2017/0051551 A1* | 2/2017 | Smart .................... E05D 13/14 |
| 2017/0281119 A1 | 10/2017 | Stroman |
| 2017/0319817 A1 | 11/2017 | Morishima et al. |
| 2017/0323630 A1 | 11/2017 | Stickney et al. |
| 2018/0078732 A1 | 3/2018 | Keshavan et al. |
| 2018/0078733 A1 | 3/2018 | Freed et al. |
| 2018/0078735 A1 | 3/2018 | Dalgleish et al. |
| 2018/0082550 A1 | 3/2018 | Read et al. |
| 2018/0236191 A1 | 8/2018 | Martin et al. |
| 2019/0029563 A1 | 1/2019 | Sels et al. |
| 2019/0030278 A1 | 1/2019 | Kremer et al. |
| 2019/0046794 A1* | 2/2019 | Goodall ................ G16H 20/40 |
| 2019/0073990 A1* | 3/2019 | Moss ................... G10K 11/175 |
| 2019/0099009 A1 | 4/2019 | Connor |
| 2020/0086076 A1 | 3/2020 | Mcelhone et al. |
| 2020/0160828 A1 | 5/2020 | Taki et al. |

OTHER PUBLICATIONS

International Search Report and Written Opinion for International Application No. PCT/US2020/018479 dated Jun. 16, 2020, 14 pp.
International Search Report and Written Opinion for International Application No. PCT/US2020/018483, dated Jun. 9, 2020, 12 pp.

* cited by examiner

DYNAMIC SOUND MASKING BASED ON MONITORING BIOSIGNALS AND ENVIRONMENTAL NOISES

Aspects of the present disclosure generally relate to closed-loop methods, devices, and systems for regulating or protecting a subject's sleep.

Disruptions to a subject's sleep may result in poor sleep and negatively affect the subject's health. Sleep disruptions may be caused by environmental or ambient noises in the sleeping environment of the subject that interrupt the subject's sleep. To try to block or compensate for such sleep disturbing noises, a static or blanket masking sound may be output in the subject's sleeping environment. However, the static masking sound is typically played throughout the entire time period the subject is sleeping at a constant, unchanging volume and frequency. Depending on the varying volumes and frequencies of the environmental noises and the subject's sleep physiology, the static masking sound may be ineffective at compensating for some sleep disturbing noises, or may itself disrupt the subject's sleep. As such, a need exists for dynamically masking individual environmental noises in a subject's sleeping environment in a manner that is tailored to the subject.

SUMMARY

Aspects of the present disclosure provide methods, apparatuses, and systems for closed-loop sleep protection and/or sleep regulation. According to an aspect, potential sleep disturbing noises are predicted and biosignal parameters of a subject are measured to dynamically mask predicted disturbing noises in the sleeping environment with active attenuation. Based on the predicted disturbing noises and the measured biosignal parameters, one or more actions are taken to regulate sleep and avoid sleep disruption by sound masking prior to or concurrently with the occurrence of the predicted disturbing noises.

According to one aspect, an audio device comprises at least one biosensor for measuring at least one biosignal parameter of a subject and a processing unit. The processing unit is configured to predict a timing of when the environmental noises will occur, and predict whether the environmental noises will disturb the subject's sleep based on the at least one measured biosignal parameter and the predicted timing of the environmental noises to identify predicted disturbing noises. The audio device further comprises at least one speaker for outputting a masking sound prior to occurrence of the predicted disturbing noises.

The processing unit may be further configured to adjust the masking sound based on the at least one measured biosignal parameter and the predicted disturbing noises. Adjusting the masking sound may comprise adjusting at least one of a spectral content of the masking sound or a sound pressure level of the masking sound. The processing unit may be configured to predict whether the environmental noises will disturb the subject's sleep based on the at least one measured biosignal parameter and the predicted timing of the environmental noises further identifies non-disturbing noises to the subject's sleep. The at least one speaker may be configured to refrain from outputting a masking sound in anticipation of the identified non-disturbing noises. The at least one speaker may be configured to gradually increase outputting the masking sound prior to the predicted disturbing noises occurring, and to gradually decrease outputting the masking sound after the predicted disturbing noises have stopped.

The audio device may further comprise at least one microphone for monitoring environmental noises in a vicinity of the audio device. The at least one microphone may be configured to monitor the environmental noises over a time period to determine reoccurring noises and to determine timing and frequency of the environmental noises. The processing unit may be further configured to receive input from the subject regarding known disturbing sounds to mask. The speaker may be further configured to output a masking sound prior to occurrence of the known disturbing sounds. The at least one biosignal parameter may comprise at least one of: a heart rate, heart rate variability, respiration rate, electroencephalogram (EEG), electrooculogram (EOG), electromyogram (EMG), or motion of the subject.

In another aspect, a method for regulating a sleep pattern of a subject comprises measuring at least one biosignal parameter of the subject while the subject is sleeping in the sleeping environment. The biosignal parameter is indicative of a current sleep condition of the subject. The method further comprises predicting whether a potentially disturbing noise will disturb the subject based on the current sleep condition and the potentially disturbing noise to identify a predicted disturbing noise, and outputting a masking sound prior to an occurrence of the predicted disturbing noise.

The method may further comprise adjusting the masking sound prior to outputting the masking sound based on the sleep condition of the subject and the predicted disturbing noise. Adjusting the masking sound may comprise adjusting at least one of: a spectral content of the masking sound or a sound pressure level of the masking sound. The masking sound may be output immediately prior to the occurrence of the predicted disturbing noise. Outputting the masking sound may comprise gradually increasing the masking sound over a first time period prior to the occurrence of the predicted disturbing noise, and gradually decreasing the masking sound over a second time period after the predicted disturbing noise has stopped.

The method may further comprise receiving, from the subject, at least one known disturbing noise to mask prior to outputting the masking sound. The method may further comprise monitoring the at least one biosignal parameter of the subject over a time period to gather historical sleep data of the subject. Predicting when the noise will disturb the subject may be further based on the historical sleep data. The method may further comprise monitoring a sleeping environment of the subject for a potentially disturbing noise over a time period via a microphone.

In yet another aspect, an audio system comprises at least one biosensor for measuring at least one biosignal parameter of a subject over a first time period. One or more values of the biosignal parameter are indicative of a sleep condition of the subject over the first time period. The audio system further comprises a processing unit configured to predict a timing of when the reoccurring ambient noises will occur, predict whether the reoccurring ambient noises will disturb the subject's sleep based on the at least one measured biosignal parameter and the predicted timing of the reoccurring ambient noises to identify predicted disturbing noises, and adjust a masking sound based on the at least one measured biosignal parameter and the predicted disturbing noises. The audio system further comprises at least one speaker configured to gradually increase outputting the masking sound prior to the predicted disturbing noises occurring, and to gradually decrease outputting the masking sound after the predicted disturbing noises are complete.

A first device may comprise the at least one biosensor. The first device may be a wearable device. The first device may further comprise the at least one speaker. The audio system may further comprise at least one microphone for monitoring ambient noises over a second time period to determine reoccurring ambient noises. A second device may comprise the at least one microphone. The second device may be a bedside unit. The second device may further comprise the at least one speaker.

The audio system may further comprise a transceiver configured to receive input from the subject regarding at least one noise that disturbed the subject's sleep. The processing unit may be configured to predict a timing of when the at least one noise will occur and further adjust the masking sound based on the predicted timing. Input from the subject may comprise a recording of the at least one noise.

All examples and features mentioned herein can be combined in any technically possible manner.

DETAILED DESCRIPTION

A sleep assistance device may include features to perform any one of preparing a subject to fall asleep, initiating the subject's sleep, protecting the subject's sleep, and selectively disrupting the subject's sleep. Aspects of the present disclosure provide methods, devices, and systems configured to collect biometric information associated with a subject and adaptively alter a sound output based on the collected information.

Figure 1:
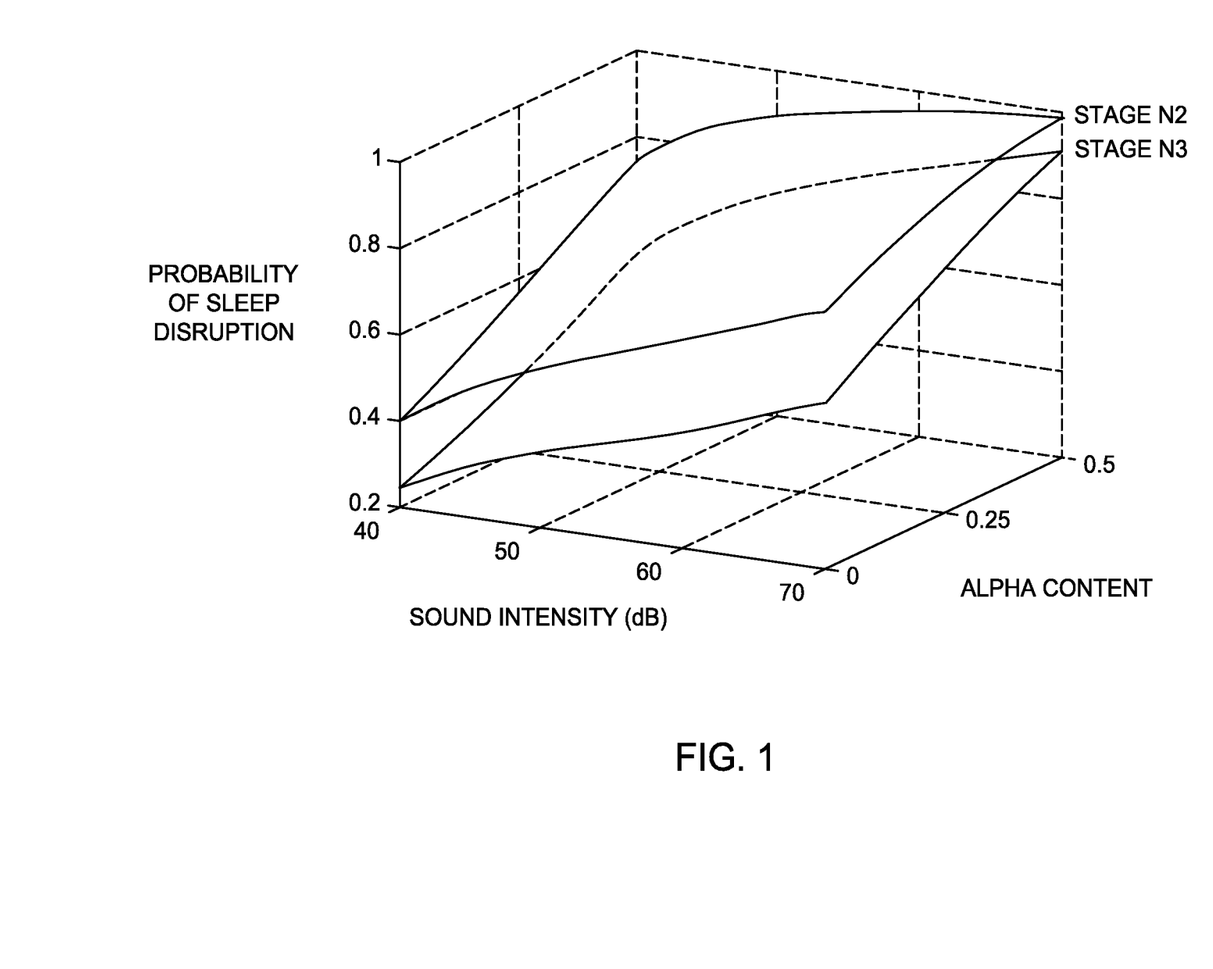
FIG. 1 illustrates an example of sleep fragility as a function of stimulus intensity and EEG alpha content.

FIG. 1 illustrates an example of sleep fragility as a function of stimulus intensity and EEG alpha content. While the example demonstrates sleep fragility as a function of stimulus intensity and EEG alpha content, other mechanisms may be used to detect sleep stages, either in combination with EEG or alone, such as EOG, accelerometer, RPM, cortical arousals, HRV, PAT/PPG, etc., as discussed further below. A subject's probability of sleep disruption is based, in part, on a condition or physiology of the subject's sleep. A condition of sleep refers to, for example, how deeply the subject is sleeping. As used herein, sleep condition may refer to as sleep physiology, sleep fragility, sleep vulnerability, or terms referring to the likelihood of sleep being disrupted.

In an example, the condition may be associated with sleep stages. Stage N3 sleep is the deepest type of non-rapid eye movement (NREM) sleep. Stage N2 sleep is lighter and more fragile than stage N3 sleep. As illustrated in FIG. 1, for a same sound intensity, a subject has an increased likelihood of sleep disruption when in stage N2 sleep than when in stage N3 sleep.

In an aspect, biometric information collected from the subject is used to approximate the subject's sleep condition. The sleep condition is used to predict the likelihood the subject's sleep may be disrupted. The effect of ambient or environmental noises on a sleeping subject varies based on the subject's sleep condition as well as the subject's individual sensitivities to such ambient or environmental noises. A same sound is less likely to disrupt a subject in deep sleep as compared to a subject whose sleep is already compromised. Sounds may be adjusted responsive to the condition of the subject's sleep so that a same sound may be masked more when the subject's sleep is compromised as compared to when the subject's sleep is less compromised.

Masking sounds are adjusted based on the subject's determined sleep condition and the environmental noise in the vicinity of the subject. The sound is altered in an effort to adaptively regulate and protect the subject's sleep. As will be described in more detail herein, the sound is altered by one or more of adjusting a sound pressure level (SPL) of a mask, adjusting a spectral content of a mask, or adjusting active noise reduction (ANR) bandwidth and level to mask (i.e., attempt to cover up the perception of) environmental noise based on the subject's determined sleep condition. According to aspects, the masking reduces the perceived loudness from the environment even if the masking does not remove the perception of environmental noise entirely. While the term "masking sound" is used throughout, the described methods, apparatuses, and systems are not limited to outputting and adjusting only masking sounds. The term "masking sound" as used herein includes other such sounds to be played in a sleeping environment, such as soothing sounds, audio therapeutics, relaxation soundtracks, entrainment soundtracks, etc.

Currently, static masking sounds such as shaped noise or ocean soundscapes attempt to help subjects fall and stay asleep; however, subjects may not enjoy listening to sound while falling asleep and subjects may be exposed to long durations of potentially harmful sound levels. Furthermore, based on the subject's changing sleep condition throughout a sleep period, these static masking sounds may disrupt the subject's sleep. Dynamically adjusting the masking properties based on the sleep condition and the environmental noise mitigates these issues by playing masking sounds to mask at reduced levels or altered spectra when able, based on sleep condition, external noise, or both at a given time. Therefore subjects are exposed to less noise, reducing potential acoustic trauma to the auditory system, as masking is played at a sound level necessary to mask external noise in view of a sleep condition. A correct amount of masking is presented to help prevent sleep disturbance.

Figure 2:
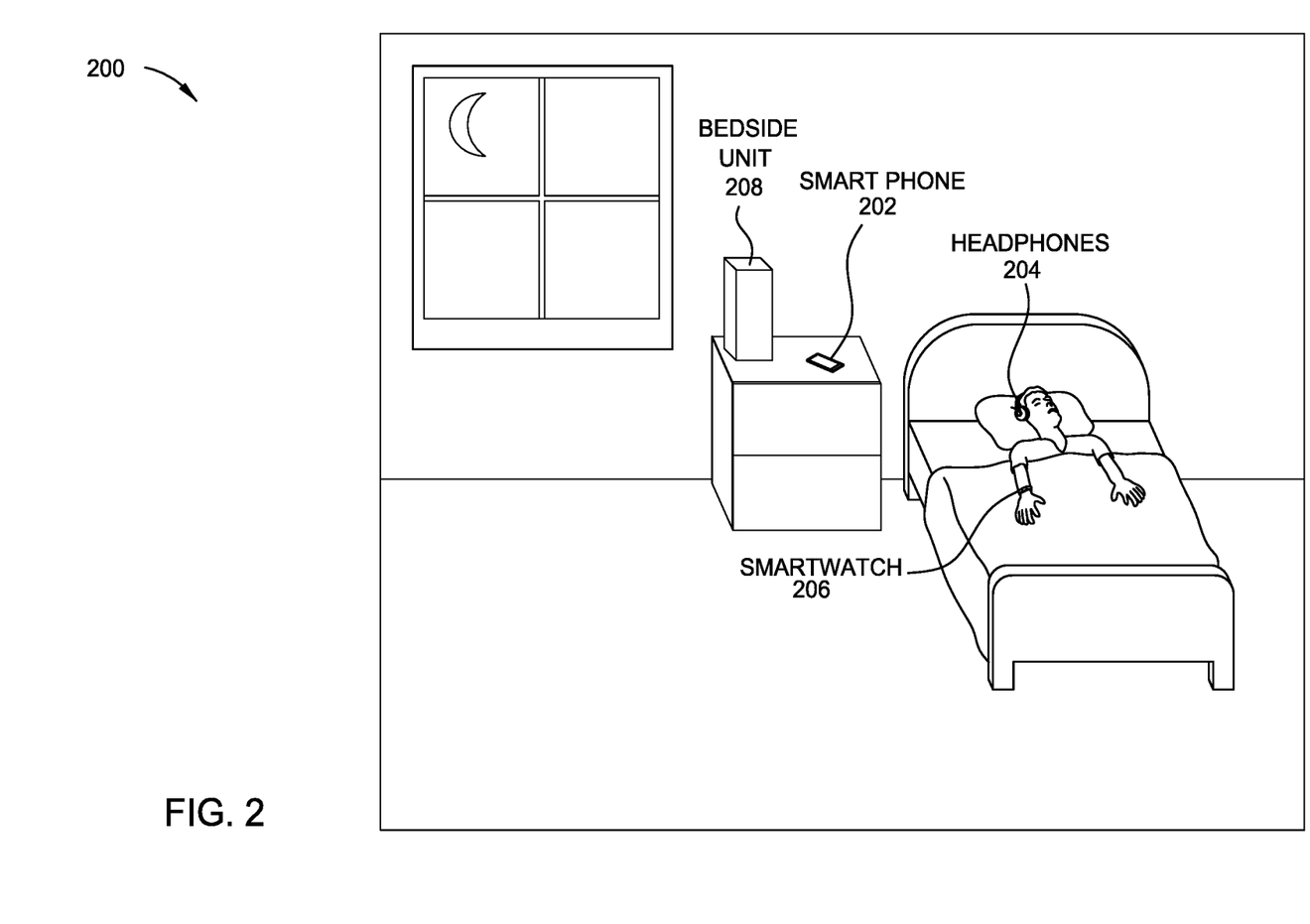
FIG. 2 illustrates an example audio system in a sleeping environment.

FIG. 2 illustrates an example audio system 200 in a sleeping environment, according to an aspect. The audio system 200 may be used to dynamically mask predicted disturbing environmental noises in the sleeping environment with active attenuation. In an example, the audio system 200 is configured to anticipate potentially disturbing noises in a subject's sleeping environment, collect biometric information of the subject, and output adjusted sounds based on the potentially disturbing noises and the biometric information collected in an effort to regulate the subject's sleep prior to or concurrently with the potentially disturbing noises occurring. The adjusted sounds may be masking sounds with an adjusted SPL and/or adjusted spectral content. Additionally or alternatively, the sounds may entrain breathing in an effort to regulate sleep. Additionally or alternatively, the audio system 200 may adjust an amount and timing of ANR based on the determined sleep condition and environmental noise in an effort to protect sleep.

The audio system 200 includes headphones 204 and a smartwatch 206, which are shown as being worn by a subject. A headphone 204 refers to a device that fits around, on, or in an ear and that radiates acoustic energy into the ear canal. Headphones 204 are sometimes referred to as earphones, earpieces, headsets, earbuds, or sport headphones, and can be wired or wireless. The headphones 204 may comprise one or more of: a processing unit, a transceiver, one or more biosensors, one or more speakers, and one or more microphones. The headphones 204 may comprise an interface configured to receive input from a subject. A smartwatch 206 may be any type of wearable computer designed to be worn on a wrist of a subject, such as a fitness tracker. The smartwatch 206 may comprise one or more of: a processing unit, a transceiver, one or more biosensors, one or more speakers, and one or more microphones. The smartwatch 206 may comprise an interface configured to receive input from a subject.

The audio system 200 further includes a bedside unit 208 and a smartphone 202. The smartphone 202 may be a mobile phone, tablet, phablet, or laptop computer. The smartphone 202 may comprise one or more of: a processing unit, a transceiver, one or more biosensors, one or more speakers, and one or more microphones. The smartphone 202 may comprise an interface configured to receive input from a subject. The bedside unit 208 may be a stationary smart device, such as a smart speaker. The bedside unit 208 may have any shape and size capable of fitting on a surface in the sleeping environment, such as a dresser, desk, or night table. For instance, the bedside unit 208 may be square, round, rectangular, pyramidal, or oval, as well as short, tall, wide, thick, or thin. The bedside unit 208 may comprise one or more of: a processing unit, a transceiver, one or more biosensors, one or more speakers, and one or more microphones. The bedside unit 208 may comprise an interface configured to receive input from a subject.

The headphones 204, the smartwatch 206, the bedside unit 208, and the smartphone 202 may each include any wired or wireless communication means suitable for use with any other device 202-208 disposed in the sleeping environment, such as WiFi, Bluetooth, Near Field Communications (NFC), USB, micro USB, or any suitable wired or wireless communications technologies known to one of ordinary skill in the art. For example, the headphones 204 may comprise one or more speakers while the bedside unit 208 comprises one or more microphones in communication with the one or more speakers of the headphones 204. Furthermore, the audio system 200 may include one or more of the devices 202-208, and is not required to include each device 202-208 shown. Thus, each device 202-208 in the audio system 200 may be optionally included, and only one device 202-208 is needed to dynamically mask environmental noises.

The devices 202-208 of the audio system 200, either alone or in combination, are configured to: monitor the sleeping environment for potentially disturbing noises, collect historical data on potentially disturbing noises in the vicinity of a subject's sleeping environment, receive input regarding potentially disturbing or non-disturbing noises, determine one or more sound parameters of the potentially disturbing noises, measure one or more biosignal parameters of a subject, collect historical data on a subject's biosignal parameters, predict a timing of when the potentially disturbing noises will occur; predict when a noise will disturb the subject's sleep, refrain from outputting a masking sound in anticipation of identified non-disturbing noises, adjust a masking sound based on the predicted disturbing noises and the measured one or more biosignal parameters in anticipation of predicted disturbing noises, and output the masking sound prior to or concurrently with a predicted disturbing noise occurring in the sleeping environment.

Figure 3:
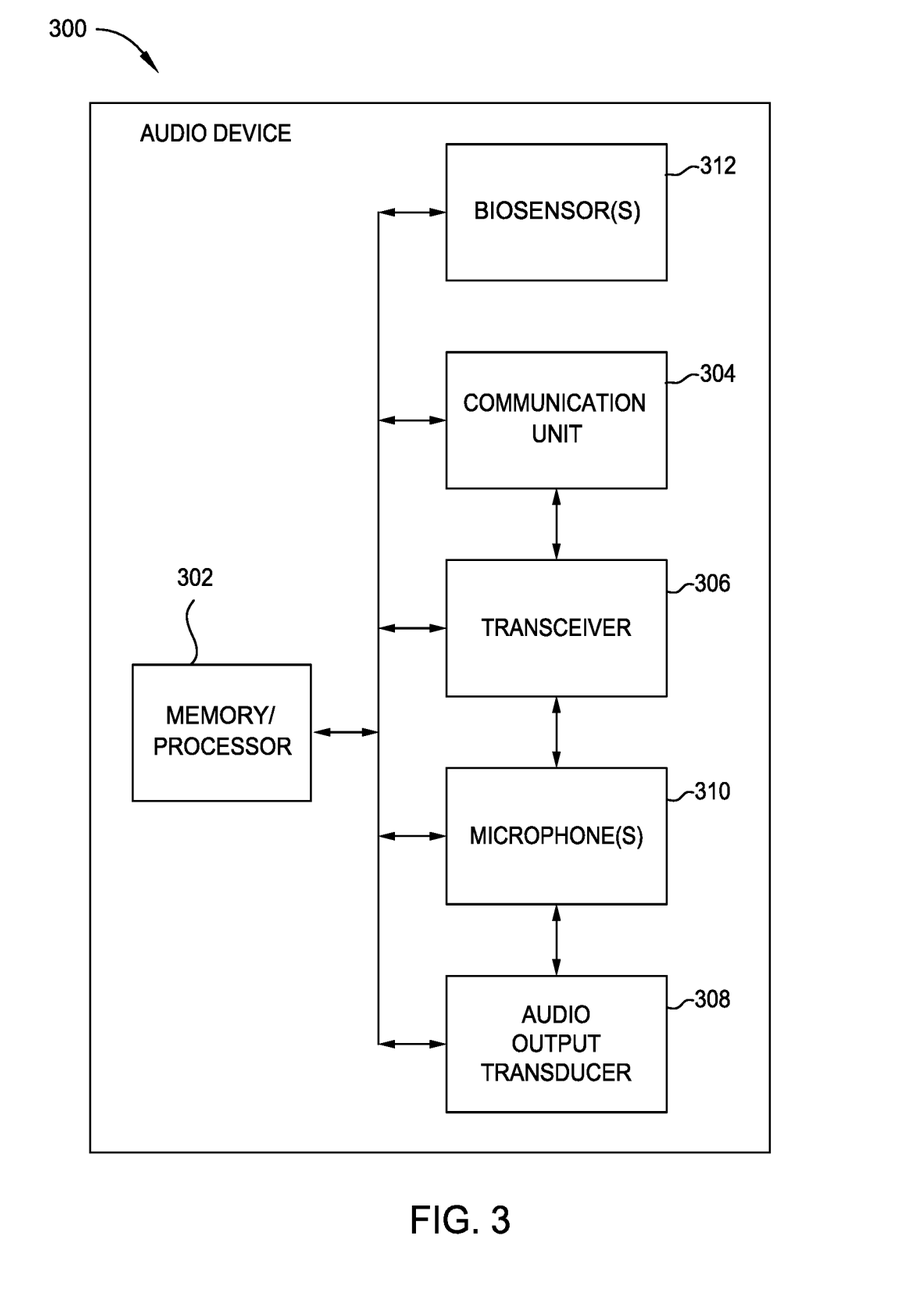
FIG. 3 illustrates example components of an audio device.

FIG. 3 illustrates example components of an audio device 300, in accordance with certain aspects of the present disclosure. According to an example, the audio device 300 is a wireless wearable audio device. The audio device 300 may be used in an audio system, such as the audio system 200 of FIG. 2. For instance, the audio device 300 may be any device 202-208 in the audio system 200 of FIG. 2. In one example, the audio device 300 is the headphones 204 of FIG. 2. The audio device 300 may be used to dynamically mask predicted disturbing environmental noises in the sleeping environment with active attenuation. In an example, the audio device 300 is configured to anticipate potentially disturbing noises in a subject's sleeping environment, collect biometric information of the subject, and output adjusted sounds based on the potentially disturbing noises and the biometric information collected in an effort to regulate the subject's sleep prior to or concurrently with the potentially disturbing noises occurring. The adjusted sounds may be masking sounds with an adjusted SPL, adjusted timing, and/or adjusted spectral content. Additionally or alternatively, the sounds may entrain breathing in an effort to regulate or protect sleep. Additionally or alternatively, the audio device 300 may adjust an amount and timing of ANR based on the determined sleep condition and environmental noise in an effort to protect sleep.

The audio device 300 includes a memory and processor 302, communication unit 304, a transceiver 306, a biosensor 312, and an audio output transducer or speaker 308. The memory may include Read Only Memory (ROM), a Random Access Memory (RAM), and/or a flash ROM. The memory stores program code for controlling the memory and processor 302. The memory and processor 302 control the operations of the audio device 300. Any or all of the components in FIG. 3 may be combined into multi-function components.

The processor 302 controls the general operation of the audio device 300. For example, the processor 302 performs process and control for audio and/or data communication. In addition to the general operation, the processor 302 outputs adjusted sounds in an effort to regulate a subject's sleep. The processor 302 is configured to measure, receive, calculate, or detect at least one biosignal parameter of the subject. The processor 302 is configured to utilize the biosignal parameter along with the subject's historical sleep data in an effort to determine a current sleep condition of the subject. The processor 302 is configured to determine, detect, or receive information associated with the environmental noise in the vicinity of the subject. The processor 302 is configured to adjust sound based on the subject's sleep condition and the environmental noise. In combination with the audio output transducer 308, the processor 302 is configured to output the adjusted sounds. The processor 302 may be further configured to receive input from a subject, such as input regarding both disturbing noises to mask and non-disturbing noises to refrain from masking. In at least one example, the processor 302 is disposed on another device in an audio system, such as a smartphone, and is in communication with the audio device 300.

In one embodiment, the processor 302 is further configured to determine when a predetermined total noise exposure level is reached or will soon be reached. In response to the total exposure level being reached, the processor 302 may be configured to cease outputting or adjusting masking sounds in response to disturbing noises in an effort to protect a subject's auditory system. In an embodiment where the processor 302 is configured to determine the total exposure level is approaching or will soon be reached, the processor 302 may be configured to reduce outputting or adjusting masking sounds in response to disturbing noises to prevent the total exposure level from being reached and to help protect a subject's auditory system.

The communication unit 304 facilitates a wireless connection with one or more other wireless devices, such as with other devices in an audio system. For example, the communication unit 304 may include one or more wireless protocol engines such as a Bluetooth engine. While Bluetooth is used as an example protocol, other communication protocols may also be used. Some examples include Bluetooth Low Energy (BLE), NFC, IEEE 802.11, WiFi, or other local area network (LAN) or personal area network (PAN) protocols. The audio device 300 may receive audio files wirelessly via the communication unit 304. Additionally or alternatively, the communication unit 304 may receive information associated with a subject's biosignal parameters, obtained via a contactless sensor. Examples of contactless sensors include a radio frequency (RF) sensor or an under-bed accelerometer.

The transceiver 306 transmits and receives information via one or more antennae to exchange information with one or more other wireless devices. The transceiver 306 may be used to communicate with other devices in an audio system, such as a bedside unit, a smartphone, and/or a smartwatch. The transceiver 306 is not necessarily a distinct component.

The audio device 300 includes the audio output transducer 308, which may be also known as a driver or speaker. In some examples, more than one output transducer is used. The transducer 308 (that may be part of a microphone) converts electrical signals into sound and converts sound into electrical signals. The transducer 308 is configured to dynamically output masking sounds. The transducer 308 outputs audio signals, including adjusted audio signals in an effort protect the subject's sleep. For example, the transducer 308 may be configured to adjust audio signals in response to a subject's biosignal parameters. In at least one example, the transducer 308 is disposed on another device in an audio system, such as a bedside unit, and is in communication with the audio device 300.

The audio device 300 optionally includes one or more microphones 310. In an aspect, the microphones 310 are used to detect environmental noises in the vicinity of the audio device 300, and convert the detected noise into electrical signals. In combination with the memory and processor 302, the microphones 310 may be configured to record, track, store, and analyze environmental noises in the vicinity of the audio device 300 over a period of time. The sound parameters or properties of the environmental noises, such as the timing, decibel level, and frequency, may be then determined to collect historical data of noises detected in the vicinity of the audio device 300 or sleeping environment. In at least one example, one or more microphones 310 are disposed on another device in an audio system, such as a bedside unit, and are in communication with the audio device 300.

The audio device 300 optionally includes one or more biosensors 312 used to determine, sense, measure, monitor, or calculate a biosignal parameter of a subject wearing the audio device 300. According to an example, the biosensor 312 is one of a photoplethysmography (PPG) sensor, electroencephalogram (EEG) sensor, electrocardiogram (ECG) sensor, electrooculogram (EOG) sensor, electromyogram (EMG) sensor, accelerometer, a microphone, or other suitable devices. The biosensor 312 may be any sensor configured to determine, sense, measure, monitor, or calculate a subject's biosignal parameter(s). The biosignal parameter(s) may comprise at least one of: a heart rate, heart rate variability, respiration rate, EEG, EOG, EMG, motion of the subject, or other suitable parameters. The biosensor 312 may be further configured to monitor a subject's biosignal parameters over a period of time to collect historical data of the biosignal parameters. The biosignal parameters may be used to determine a sleep condition or sleep physiology of the subject. Based on the sleep condition, an arousal threshold may be determined. The sleep condition may be determined based on one or more of personalized sleep data or historical sleep data collected using a subset of society, or both.

According to an aspect when the audio device 300 is headphones, only one earpiece (ear tip, ear cup) of the audio device 300 includes the biosensor 312. In an aspect, neither earpiece includes a biosensor 312. Instead, a biosensor 312, not on the audio device 300, may remotely detect a biosignal parameter of the subject. In an example, the biosensor 312 detects fluctuations in small arteries (i.e., arterioles) with a sensor, for example, on the finger to determine blood vessel dynamics, which may help to determine the subject's sleep fragility. In an example, the biosensor 312 detects a subject's heartrate or heart rate variability (HRV) with a sensor disposed on the wrist, such as by utilizing a smartwatch. In an example, the biosensor 312 may be a contactless biosensor. The contactless biosensor is configured to report detected biosignal parameters to the processor 302, for example, via the communication unit 304. In at least one example, the biosensor 312 is disposed on another device in an audio system, such as a smartwatch, and is in communication with the audio device 300.

FIG. 3 illustrates communication between certain modules of an example audio device 300; however, aspects of the disclosure are not limited to the specific illustrated example. According to aspects, any module 302-312 is configured to communicate with any other module in the audio device 300. In one example, all modules 302-312 are connected to and communicate with each other.

Figure 4:
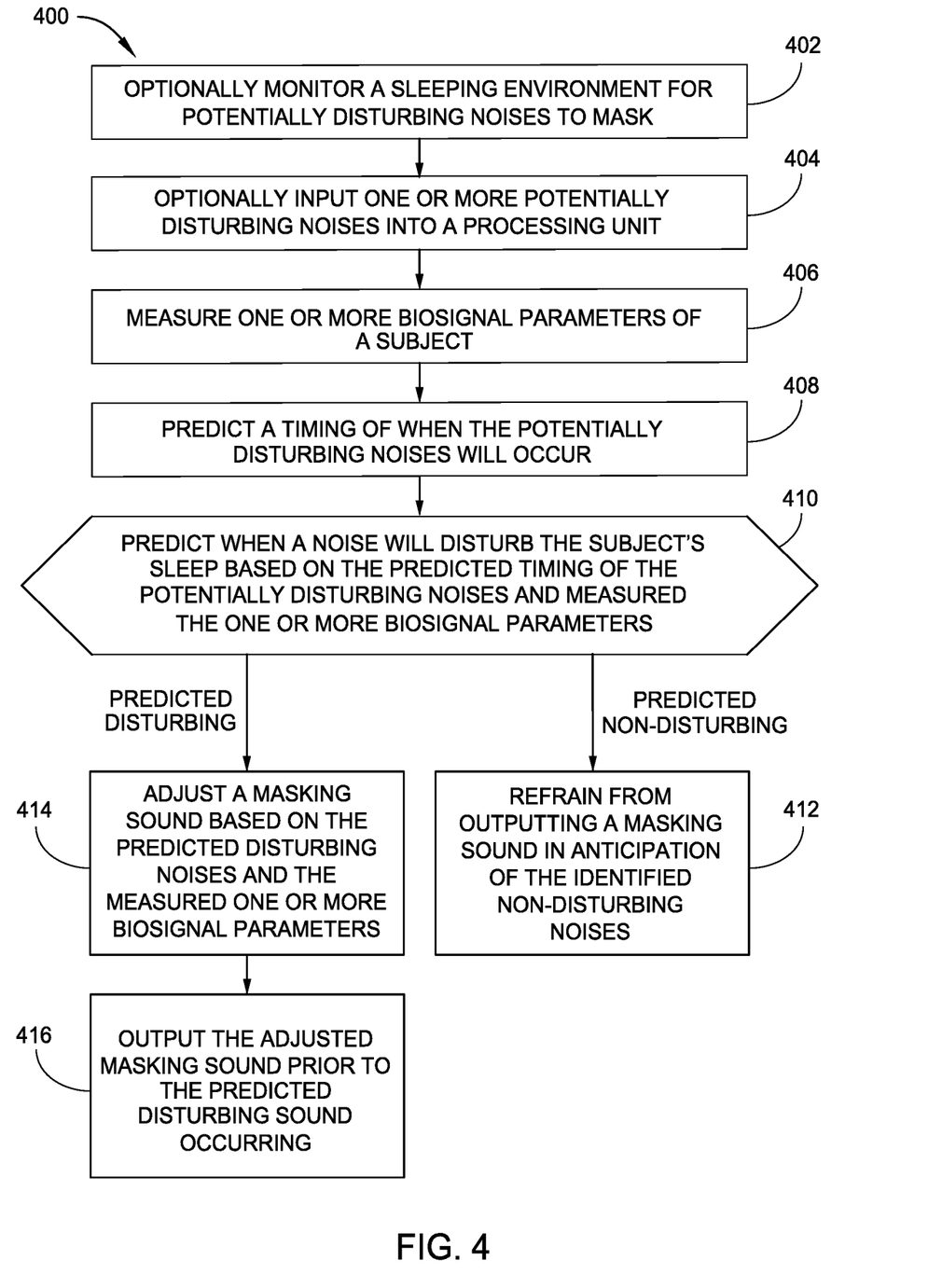
FIG. 4 illustrates an example method for dynamically and proactively masking potential sleep disturbing noises in a sleeping environment.

FIG. 4 illustrates an example method 400 for dynamically and proactively masking potential sleep disturbing noises in a sleeping environment. Method 400 may be implemented utilizing the audio system 200 of FIG. 2 and/or the audio device 300 of FIG. 3.

At 402, a sleeping environment is optionally monitored for potential sleep disturbing noises. The sleeping environment may be monitored using a microphone, such as the microphone 310 of FIG. 3. The sleeping environment may be monitored over a period of time to determine reoccurring noises and to determine sound parameters of the detected environmental noises. The microphone may detect various sound parameters of the detected noises, such as the decibel level, the onset and offset, the rate, the timing, and the frequency. In combination with a memory and processor, the microphone may detect environmental noises over a period of time, allowing historical data of the noises in the subject's sleeping environment to be collected and analyzed. The historical data of the noises in the subject's sleeping environment may be used to refine the dynamic masking via a learning algorithm.

At 404, one or more potentially disturbing noises are optionally input into a processing unit. A processing unit, such as the processor 302 of FIG. 3, or a smart device, such as the smartphone 202 or smartwatch 206 of FIG. 2, may be configured to receive input from the subject regarding at least one noise that is known to disturb the subject's sleep. The subject may further input one or more non-disturbing noises that the subject does not wish be masked. For example, the subject may wish to hear a baby crying, and may input a baby's crying as a non-disturbing noise to refrain from masking. Additionally, the subject may input various time periods of when to mask or refrain from masking environmental noises. The subject inputting potentially disturbing noises to mask and non-disturbing noises to refrain from masking allows that subject's individual sensitivities and preferences to be taken into consideration, permitting the subject to tailor the dynamic masking as desired.

Such input from the subject may be from a list of pre-selected options, a noise the subject records, or a noise known to occur around the same time in the vicinity of the subject's sleeping environment. The pre-selected options may be a list of noises that are known to either disturb or not disturb sleep selected by a manufacture, disturbing or non-disturbing noises recorded by the subject, or a list of disturbing or non-disturbing noises generated based on the location of the subject's sleep environment. For instance, other users located geographically near the subject's sleeping environment may upload or input noises that were disturbing or non-disturbing to that user's sleep. The subject may then browse the list of user-input noises and select one or more noises the subject predicts will disturb their sleep to mask, or one or more noises the subject predicts will be non-disturbing noises to refrain from masking. In another example, the subject may input, select, or download a schedule of known sleep disturbing noises, such as a train or flight schedule if the subject's sleeping environment is located near train tracks, a train station, an airport, a bus route, etc.

At 406, one or more biosignal parameters of a subject are measured. The biosignal parameters may be measured or monitored using a biosensor, such as the biosensor 312 of FIG. 3. The one or more biosignal parameters may comprise at least one of: a heart rate, heart rate variability, respiration rate, EEG, EOG, EMG, motion of the subject, or other suitable parameters. One or more values of the biosignal parameters may be indicative of a sleep condition or sleep physiology of the subject over a time period. Based on the sleep condition or physiology, an arousal threshold may be determined. The sleep condition or physiology may be determined based on one or more of personalized sleep data or historical sleep data collected using a subset of society, or both.

In at least one example, the one or more biosignal parameters of the subject are monitored over a time period and analyzed to collect historical sleep data of the subject. For example, the subject's biosignal parameters may be measured every time the subject sleeps in the sleeping environment for several days, such as a week or a month. The subject's biosignal parameters may be analyzed via a learning algorithm each time the biosignal parameters are measured or uploaded. The analyzed biosignal parameters may provide information regarding the subject's threshold to different kinds of environmental noises or masking sounds, allowing the dynamic masking to be uniquely tailored or fine-tuned to the subject. The analyzed biosignal parameters may further provide information regarding the subject's sleep patterns, such as waking or sleep stage cycles or reoccurring events taking place at approximately the same time during a subject's sleep cycle, which may be used to help predict when environmental noises will disturbing the subject's sleep. Additionally, the historical sleep data of the subject may be used in combination with the historical environmental noise data gathered in operation 402 and/or with the input received in operation 404. Thus, the subject's unique stages of sleep relative to different sounds in the sleeping environment may be taken into consideration.

At 408, a timing of when the potentially disturbing noises will occur is predicted. Predicting the timing of when the potentially disturbing noises will occur may be based on the determined reoccurring noises of operation 402 or on the input of operation 404. Additionally, predicting the timing may include predicting a pattern, interval, frequency, volume or decibel level, and/or onset/offset of the potentially disturbing noise. Predicting the timing of the potentially disturbing noises enables the potentially disturbing noises to be anticipated, and as such, enables the masking noise to be dynamic. In an aspect, the potentially disturbing noises are predicted to have already begun, in which case method 400 proceeds to 410.

At 410, a prediction of when a noise will disturb the subject's sleep is made based on the predicted timing of the potentially disturbing noises and the measured one or more biosignal parameters. The prediction may be further based on the sleep condition of the subject and the historical sleep data of the subject. As described above with reference to FIG. 1, a subject's sleep condition is used to predict the likelihood the subject's sleep may be disrupted, and the effect of environmental noises on a sleeping subject varies based on the subject's sleep condition. Thus, depending on the biosignal parameters and the sleep condition, an environmental noise may be predicted to be a non-disturbing at one time, but as a disturbing noise at another time. If a noise is not predicted to be a sleep disturbing noise, the noise is identified as a non-disturbing noise, and method 400 proceeds to 412. At 412, a masking sound is refrained from being output in anticipation of the identified non-disturbing noise. In one embodiment, the masking sound is refrained from increasing in volume, but may continue to be output at a lower volume or level when noises are identified as non-disturbing.

If a noise is predicted to disturb the subject's sleep, method 400 proceeds to 414. At 414, a masking sound is dynamically adjusted based on the parameters of the predicted disturbing noises and the measured one or more biosignal parameters. The masking sound may further be adjusted based on the sleep condition of the subject, the arousal threshold, and/or the historical sleep data of the subject. Adjusting the masking sound may comprise adjusting a masking sound that is already being output in the sleeping environment, or adjusting or setting the parameters of a masking sound that is to be output in the sleeping environment. Adjusting the masking sound may comprise adjusting at least one of: a spectral content of the masking sound or a SPL of the masking sound. Adjusting the masking noise may further include adjusting the frequency, volume, timing, and rate of the masking sound. For example, if the disturbing noise is relatively quiet, such as around 40 dB, and the subject is in a deep sleep stage, such as stage N3 sleep, the masking noise may be adjusted to a lower volume to compensate for the disturbing noise. Thus, even if the same predicted disturbing noise occurs at the same time every night, the masking noise output may be different depending on the biosignal parameters, the sleep condition/arousal threshold of the subject at that particular time, and data learned or gathered via the learning algorithm.

At 416, the adjusted masking sound is output prior to or concurrently with the predicted disturbing sound occurring. A speaker may be used to output the adjusted masking sound, such as the audio output transducer 308 of FIG. 3. The speaker may be configured to gradually increase outputting the masking sound prior to the predicted disturbing noise occurring, and to gradually decrease outputting the masking sound after the predicted disturbing noise has ceased. The speaker may be further configured to dynamically and continuously adjust the output of the masking noise if the disturbing noise is a fluctuating, oscillating, or pulsating noise. The speaker may be further configured to output the masking sound immediately prior to or concurrently with the occurrence of the predicted disturbing noise. For example, if a predicted disturbing noise starts off quietly and becomes louder, such as a passing train, the speaker may be configured to output the masking sound immediately prior to or concurrently with the predicted disturbing noise beginning. The speaker may be further configured to dynamically and continuously adjust the output of the masking noise in response to disturbing noises occurring in real-time in the sleeping environment, such as adjusting the masking noise in response to a changing volume or frequency of the disturbing noise.

By utilizing the method and apparatus described above for dynamically and proactively masking potential sleep disturbing noises in a sleeping environment, a subject's sleep may be regulated and/or protected by reducing sleep disruptions. Adjusting a masking noise based on the parameters of the predicted disturbing noise and the subject's biosignal parameters allows the masking to be individually and uniquely tailored to the needs of the subject. Furthermore, dynamically masking environmental noises prior to or concurrently with the occurrence of the predicted disturbing noise enables the noise to be masked in an efficient and effective manner.

According to aspects, methods of protecting sleep are cut off or stopped based on a subject's selections. The subject may select one or more sounds, notices, or alerts which are not to be masked, or which are to be identified as non-disturbing noises. For example, the subject may wish to hear fire alarms, security system notifications, a phone ringing, a crying baby, a doorbell, and/or any other audible notification or alarm. The subject may program the audio device or audio system to recognize these desired sounds. The audio device or audio system may refrain from masking these detected sounds or from applying ANR in the presence of these detected sounds.

According to aspects, the subject may program the audio device or audio system to recognize undesired sounds which may be specific to the subject's environment. In an example, the subject may program the audio device or audio system to recognize a crying baby, a snoring companion, or garbage trucks. The audio device or audio system may mask or noise-cancel (in examples, partially noise-cancel) these detected sounds.

According to an aspect, the desired and undesired sounds may be programmed by any combination of selecting these sounds from a library or recording real-life examples of the sounds for input to the audio device or audio system. The subject may categorize sounds as desired/non-disturbing or undesired/disturbing. The audio device or audio system is configured to analyze components of the ambient noise to identify the selected sounds and categorize them as desired or undesired sounds based on the subject's selections. The audio device or audio system masks the undesired sounds or applies a higher level of ANR for undesired sounds and does not mask the desired sounds or applies a lower level of ANR for desired sounds. Accordingly, selected portions of the ambient noise are selectively masked or are not masked.

In addition to categorizing sounds as desired and undesired, the subject can identify sounds that should be enhanced. For example, a subject may need to hear a crying baby or any other audible notification or alarm at certain times. The subject may program the audio device or audio system to recognize these sounds and enhance them upon detection.

In the preceding, reference is made to aspects presented in this disclosure. However, the scope of the present disclosure is not limited to specific described aspects. Aspects of the present disclosure may take the form of an entirely hardware embodiment, an entirely software embodiment (including firmware, resident software, micro-code, etc.) or an embodiment combining software and hardware aspects that may all generally be referred to herein as a "component," "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples of a computer readable storage medium include: an electrical connection having one or more wires, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the current context, a computer readable storage medium may be any tangible medium that can contain, or store a program.

The flowchart and block diagrams in the figures illustrate the architecture, functionality and operation of possible implementations of systems, methods and computer program products according to various aspects. In this regard, each block in the flowchart or block diagrams may represent a module, segment or portion of code, which comprises one or more executable instructions for implementing the specified logical function(s). In some implementations the functions noted in the block may occur out of the order noted in the figures. For example, two blocks shown in succession may, in fact, be executed substantially concurrently, or the blocks may sometimes be executed in the reverse order, depending upon the functionality involved. Each block of the block diagrams and/or flowchart illustrations, and combinations of blocks in the block diagrams and/or flowchart illustrations can be implemented by special-purpose hardware-based systems that perform the specified functions or acts, or combinations of special purpose hardware and computer instructions.

The invention claimed is:

1. An audio device, comprising:
at least one biosensor configured to measure at least one biosignal parameter of a subject;
a processing unit in communication with a microphone of another device, the microphone operable to capture environmental noises in a vicinity of the audio device;
a non-volatile memory configured to store a history of the at least one biosignal parameter of the subject and the environmental noises over a period of time;
wherein the processing unit is configured to:
determine timings of sleep disruptions of the subject based on the at least one biosignal parameter;
analyze the stored history of the at least one biosignal parameter of the subject and the environmental noises over the period of time to determine how the subject reacted to decibel levels, frequencies, and a recorded timing of the environmental noises;

predict, using the determined timings of sleep disruptions of the subject and the at least one biosignal parameter measured by the at least one biosensor, a future timing of an upcoming instance of the environmental noises having similar values to the decibel levels, the frequencies and the recorded timing;

predict the upcoming instance of the environmental noises will disrupt the subject's sleep based on the at least one biosignal parameter measured and the predicted future timing of the upcoming instance of the environmental noises; and based, at least in part, on the predicted upcoming instance of the environmental noise that will disrupt the subject's sleep and the analysis of the stored history, adjust a masking sound that protects the subject's sleep from being disrupted; and at least one speaker configured to output the adjusted masking sound prior to occurrence of the predicted upcoming instance of the environmental noises.

2. The audio device of claim 1, wherein the processing unit is further configured to adjust the masking sound based on the at least one measured biosignal parameter and the predicted upcoming instance of environmental noises, and wherein adjusting the masking sound comprises adjusting at least one of: a spectral content of the masking sound or a sound pressure level of the masking sound.

3. The audio device of claim 1, wherein:
the processing unit configured to predict whether the environmental noises will disturb the subject's sleep based on the at least one measured biosignal parameter and the predicted timing of the environmental noises further identifies non-disturbing noises to the subject's sleep, and
the at least one speaker is configured to refrain from outputting a masking sound in anticipation of the identified non-disturbing noises.

4. The audio device of claim 1, wherein the at least one speaker is configured to gradually increase outputting the masking sound prior to the predicted upcoming instance of environmental noises occurring, and to gradually decrease outputting the masking sound after the predicted upcoming instance of environmental noises have stopped.

5. The audio device of claim 1, wherein:
the processing unit is further configured to receive input from the subject regarding known disturbing sounds to mask, and
the at least one speaker is further configured to output a masking sound prior to occurrence of the predicted upcoming instance of the environmental noises when the environmental noises are the known disturbing sounds.

6. The audio device of claim 1, wherein the at least one biosignal parameter comprises at least one of: a heart rate, heart rate variability, respiration rate, electroencephalogram (EEG), electrooculogram (EOG), electromyogram (EMG), or motion of the subject.

7. A method for regulating a sleep pattern of a subject, comprising:
measuring at least one biosignal parameter of the subject while the subject is sleeping in a sleeping environment, wherein the biosignal parameter is indicative of a current sleep condition of the subject;
capturing environmental noises in a vicinity of an audio device;
storing a history of the at least one biosignal parameter of the subject and the environmental noises over a period of time;

determining timings of sleep disruptions of the subject based, at least in part, on the stored history of the at least one biosignal parameter of the subject and the environmental noises over the period of time;

analyzing the stored history of the at least one biosignal parameter of the subject and the environmental noises over the period of time to determine how the subject reacted to decibel levels, frequencies, and a recorded timing of the environmental noises;

predicting, using the determined timings of sleep disruptions of the subject and the at least one biosignal parameter, whether a potentially disturbing noise will disturb the subject based on the current sleep condition and the potentially disturbing noise having similar values to the decibel levels, the frequencies, and the recorded timing; and adjusting and outputting a masking sound to maintain the current sleep condition based on the analyzing of the stored history prior to an occurrence of the predicted disturbing noise.

8. The method of claim 7, further comprising:
adjusting the masking sound prior to outputting the masking sound based on the sleep condition of the subject and the prediction of whether the potentially disturbing noise will disturb the subject based on the current sleep condition and the potentially disturbing noise, wherein adjusting the masking sound comprises adjusting at least one of: a spectral content of the masking sound or a sound pressure level of the masking sound.

9. The method of claim 7, wherein the masking sound is output immediately prior to the subject being disturbed by the potentially disturbing noise.

10. The method of claim 7, wherein outputting the masking sound comprises gradually increasing the masking sound over a first time period prior to the potentially disturbing noise, and gradually decreasing the masking sound over a second time period after the potentially disturbing noise has stopped.

11. The method of claim 7, further comprising:
receiving, from the subject, at least one known disturbing noise to mask prior to outputting the masking sound.

12. The method of claim 7, further comprising: monitoring the sleeping environment of the subject for a potentially disturbing noise over a time period via a microphone.

13. An audio system, comprising:
at least one biosensor configured to measure at least one biosignal parameter of a subject over a first time period, wherein one or more values of the at least one biosignal parameter are indicative of a sleep condition of the subject over the first time period;
a processing unit in communication with a microphone of a first device, the microphone operable to capture environmental noises in a vicinity of the audio device, wherein the processing unit is configured to:
determine timings of sleep disruptions of the subject based, at least in part, on the one or more values of the at least one biosignal parameter in the first time period and the environmental noises over the first time period;
analyze the at least one biosignal parameter of the subject and the environmental noises over the first time period to determine how the subject reacted to decibel levels, frequencies, and a recorded timing of the environmental noises;
identifying reoccurring ambient noises from the decibel levels, the frequencies, and the recorded timing of the environmental noises;

predict a future timing of when the reoccurring ambient noises will occur;
predict whether the reoccurring ambient noises will disturb the subject's sleep based on the at least one measured biosignal parameter and the predicted future timing of the reoccurring ambient noises to identify predicted disturbing noises having similar values to the decibel levels and the frequencies; and
adjust a masking sound based on the at least one measured biosignal parameter, the predicted disturbing noises, and the analysis of the at least one biosignal parameter of the subject and the environmental noises; and
at least one speaker configured to gradually increase outputting the masking sound prior to the predicted disturbing noises occurring, and to gradually decrease outputting the masking sound after the predicted disturbing noises are complete.

14. The audio system of claim 13, wherein the first device comprises the at least one biosensor, and wherein the first device is a wearable device.

15. The audio system of claim 14, wherein the first device further comprises the at least one speaker.

16. The audio system of claim 14, further comprising an additional microphone for monitoring ambient noises over a second time period to determine the reoccurring ambient noises.

17. The audio system of claim 16, further comprising a second device, wherein the second device comprises the additional microphone, and wherein the second device is a bedside unit.

18. The audio system of claim 17, wherein the second device further comprises the at least one speaker.

19. The audio system of claim 13, further comprising:
a transceiver configured to receive input from the subject regarding at least one noise that disturbed the subject's sleep,
wherein the processing unit is configured to predict a timing of when the at least one noise will occur and further adjust the masking sound based on the predicted timing.

20. The audio system of claim 19, wherein input from the subject comprises a recording of the at least one noise.

* * * * *